US012376791B2

(12) United States Patent
Harutyunyan et al.

(10) Patent No.: US 12,376,791 B2
(45) Date of Patent: Aug. 5, 2025

(54) ELECTRONIC TEXTILES

(71) Applicant: Honda Motor Co., Ltd., Tokyo (JP)

(72) Inventors: Avetik Harutyunyan, Santa Clara, CA (US); Hiroshi Tsujino, San Jose, CA (US)

(73) Assignee: Honda Motor Co., LTD, Tokyo (JP)

( * ) Notice: Subject to any disclaimer, the term of this patent is extended or adjusted under 35 U.S.C. 154(b) by 476 days.

(21) Appl. No.: 17/570,025

(22) Filed: Jan. 6, 2022

(65) Prior Publication Data

US 2022/0225691 A1    Jul. 21, 2022

Related U.S. Application Data

(60) Provisional application No. 63/139,665, filed on Jan. 20, 2021.

(51) Int. Cl.
*A61B 5/00* (2006.01)
*A61B 5/0225* (2006.01)
(Continued)

(52) U.S. Cl.
CPC .......... *A61B 5/6812* (2013.01); *A61B 5/0225* (2013.01); *A61B 5/27* (2021.01);
(Continued)

(58) Field of Classification Search
CPC ....... A61B 5/6812; A61B 5/0225; A61B 5/27; A61H 11/00; A61H 2011/005;
(Continued)

(56) References Cited

U.S. PATENT DOCUMENTS 7,144,830 B2    12/2006    Hill et al.
7,348,645 B2    3/2008     Xu
(Continued)

FOREIGN PATENT DOCUMENTS

CN    205072851 U    3/2016
CN    107106054 A    8/2017
(Continued)

OTHER PUBLICATIONS

"Davidson, Z., Shahsavan, H., Aghakhani, A., Guo, Y., Hines, L., Xia, Y., Yang, S., Sitti, M., Monolithic shape-programmable dielectric liquid crystal elastomer actuators, 2019, https://arxiv.org/abs/1904.09606" (Year: 2019).*
(Continued)

*Primary Examiner* — James M Kish
*Assistant Examiner* — Laura Hodge
(74) *Attorney, Agent, or Firm* — Patterson + Sheridan, LLP

(57) ABSTRACT

Aspects of the present disclosure generally relate to electronic textiles and more specifically to self-sustaining, interactive electronic textiles, to systems incorporating such electronic textiles, and to uses thereof. In an embodiment, a system to assist with an intended motion of a user is provided. The system includes one or more processors, and an electronic textile. The electronic textile includes a textile substrate, an actuator coupled to the textile substrate, a sensor coupled to the textile substrate, and a battery coupled to the textile substrate, the battery electrically coupled to a conductive yarn, the conductive yarn further electrically coupled to the actuator and the sensor. Embodiments also include a system to assist with blood circulation of a user and a method of assisting blood circulation of a user.

20 Claims, 2 Drawing Sheets

(51) Int. Cl.
| | |
|---|---|
| *A61B 5/27* | (2021.01) |
| *A61H 11/00* | (2006.01) |
| *A61H 99/00* | (2006.01) |
| *D03D 1/00* | (2006.01) |
| *H01M 4/62* | (2006.01) |
| *H05K 1/03* | (2006.01) |

(52) U.S. Cl.
CPC ............ *A61B 5/6824* (2013.01); *A61H 11/00* (2013.01); *A61H 99/00* (2013.01); *D03D 1/0088* (2013.01); *H01M 4/62* (2013.01); *H05K 1/038* (2013.01); *A61H 2011/005* (2013.01); *A61H 2201/1207* (2013.01); *A61H 2201/165* (2013.01); *A61H 2209/00* (2013.01); *D10B 2401/16* (2013.01); *D10B 2501/04* (2013.01); *D10B 2509/00* (2013.01)

(58) Field of Classification Search
CPC ..... H01M 4/62; H05K 1/038; D10B 2401/16; D10B 2501/04; D10B 2509/00
See application file for complete search history.

(56) References Cited

U.S. PATENT DOCUMENTS

| | | | |
|---|---|---|---|
| 7,683,643 | B2 | 3/2010 | Qi et al. |
| 7,770,473 | B2 | 8/2010 | Von Lilienfeld-Toal et al. |
| 9,232,637 | B2 | 1/2016 | Van Abeelen et al. |
| 9,907,473 | B2 | 3/2018 | Tran |
| 2010/0256475 | A1 | 10/2010 | Chiang |
| 2013/0211208 | A1 | 8/2013 | Varadan et al. |
| 2013/0281795 | A1 | 10/2013 | Varadan |
| 2013/0321168 | A1 | 12/2013 | Mahony et al. |
| 2015/0233858 | A1 | 8/2015 | Strickland et al. |
| 2016/0165988 | A1* | 6/2016 | Glasgow ............... A41H 1/02 703/11 |
| 2016/0278444 | A1 | 9/2016 | Jordan et al. |
| 2017/0119314 | A1* | 5/2017 | Just ...................... A61B 5/6843 |
| 2018/0024622 | A1* | 1/2018 | Cobanoglu ........... A41D 1/005 348/208.14 |
| 2018/0116561 | A1 | 5/2018 | Jo et al. |
| 2018/0294058 | A1 | 10/2018 | Bostick et al. |
| 2019/0036103 | A1 | 1/2019 | Pierce et al. |
| 2019/0051904 | A1* | 2/2019 | Zhamu ................ H01M 10/058 |
| 2020/0083560 | A1 | 3/2020 | Harutyunyan et al. |
| 2020/0136105 | A1* | 4/2020 | Zhi ....................... H01M 10/02 |
| 2020/0243807 | A1 | 7/2020 | Harutyunyan |
| 2020/0283295 | A1 | 9/2020 | Harutyunyan |
| 2021/0368910 | A1* | 12/2021 | Moller .................. A43B 7/146 |

FOREIGN PATENT DOCUMENTS

| | | | | |
|---|---|---|---|---|
| CN | 108673518 | A | | 10/2018 |
| CN | 210009015 | U | | 2/2020 |
| DE | 102005033643 | A1 | | 2/2007 |
| JP | 5135757 | B2 | | 2/2013 |
| JP | 2018183455 | A | * | 11/2018 |
| KR | 200423283 | Y1 | | 8/2006 |
| KR | 101369575 | B1 | | 3/2014 |
| WO | WO-2010058360 | A1 | * | 5/2010 ............. G09F 21/02 |
| WO | WO-2017165435 | A2 | * | 9/2017 ............... D02G 3/26 |

OTHER PUBLICATIONS

Wang et al., "High-Performance Biscrolled Mxene/Carbon Nanotube Yarn Supercapacitors" Small 2018, 14, 1802225; 10 pages.

Levitt et al., "Electrospun Mxene/carbon nanofibers as supercapacitor electrodes" J. Mater. Chem. A, 2019, 7, 269; 9 pages.

Weng et al., "Winding aligned Carbon Nanotube Composite Yams into Coaxial Fiber Full Batteries with High Performances" Nano Lett. 2014, 14, 3432-3438.

Qu et al., "Flexible fibers batteries for applications in smart textiles" Jan. 2013, Materials Research Society symposia proceedings, Materials Research Society, 1489, DOI:10.1557/opl.2013.913; 10 pages.

Haines et al., "Artificial Muscles from Fishing Line and Sewing Thread" Feb. 21, 2014, vol. 343, Science; 6 pages.

Roach et al., "Long Liquid Crystal Elastomer Fibers with Large Reversible Actuation Strains for Smart Textiles and Artificial Muscles" ACS Appl. Mater. Interfaces 2019, 11, 19514-19521.

Zhang, Luhui et al., "Fiber and fabric solar celss by directly weaving carbon nanotube yams with CdSe nanowire-based electrodes" Nanoscale, 2012, 4, 4954; 6 pages.

Zhang, Sen et al., "Porous, Platinum Nanoparticle-Adsorbed Carbon Nanotube Yams for Efficient Fiber Solar Cells" ACS Nano, 2012, vol. 6, No. 8, 7191-7198.

Liu et al., "Solid-State, Polymer-Based Fiber Solar Cells with Carbon Nanotube Electrodes" ACS Nano, 2012, vol. 6, No. 12, 11027-22034.

Huang et al., "Weavable, Conductive Yarn-Based NiCo//Zn Textile Battery with High Energy Density and Rate Capability" ACS Nano 2017, 11, 8953-8961.

Lee et al., "Biscrolled Carbon Nanotube Yarn Structured Silver-Zinc Battery" Scientific Reports, (2018) 8:11150, DOI:10.1038/s41598-018-29266-0; 8 pages.

* cited by examiner

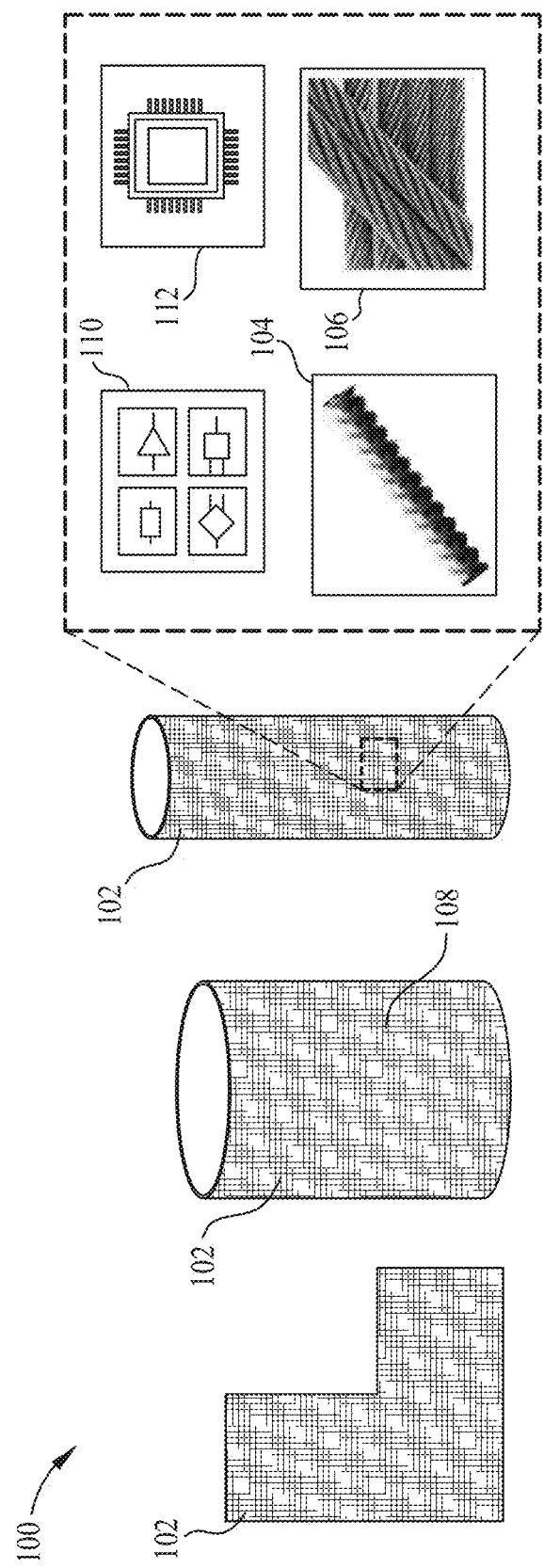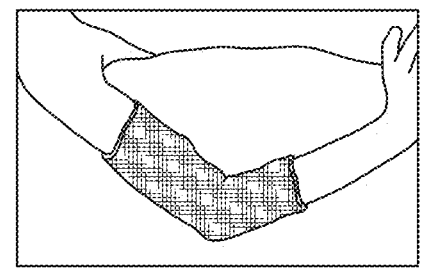
FIG. 1A
FIG. 1B

ELECTRONIC TEXTILES

CROSS-REFERENCE TO RELATED APPLICATIONS

This application claims benefit to U.S. Provisional Application No. 63/139,665, filed on Jan. 20, 2021, which is herein incorporated by reference in its entirety.

FIELD

Aspects of the present disclosure generally relate to electronic textiles and more specifically to self-sustaining, interactive electronic textiles, to systems incorporating such electronic textiles, and to uses thereof.

BACKGROUND

When electronic components are integrated into textiles, new applications emerge such as functional textiles (or smart textiles) and wearable electronics, collectively known as wearables. Wearables typically take two forms—passive and motorized. The passive type defines those wearables that are used to, e.g., protect an injury, such as a knee brace, and exhibit little-to-no mobility workload. Motorized wearables, in contrast, make motion and exhibit high-mobility workload. Examples of motorized wearables include exoskeletons.

Currently, however, there is a need for wearables that support or assist in, e.g., the intended motion of the person and that regulate blood circulation, among other functions. There is also a need for an integrated platform where sensors, power storage, and actuators, are embedded within a single electronic textile.

SUMMARY

Aspects of the present disclosure generally relate to electronic textiles and more specifically to self-sustaining, interactive electronic textiles, to systems incorporating such electronic textiles, and to uses thereof.

In an aspect, a system to assist with an intended motion of a user is provided. The system includes one or more processors, and an electronic textile. The electronic textile includes a textile substrate, an actuator coupled to the textile substrate, a sensor coupled to the textile substrate, and a battery coupled to the textile substrate, the battery electrically coupled to a conductive yarn, the conductive yarn further electrically coupled to the actuator and the sensor.

In another aspect, a system to assist with blood circulation of a user is provided. The system includes one or more processors, and a wearable electronic textile. The wearable electronic textile includes a textile substrate, a contractable or expandable actuator coupled to the textile substrate, a sensor coupled to the textile substrate, and a battery coupled to the textile substrate, the battery electrically coupled to a conductive yarn, the conductive yarn further electrically coupled to the actuator and the sensor.

In another aspect, a method of assisting blood circulation of a user is provided. The method includes analyzing sensor data from a sensor coupled to a textile substrate of a wearable electronic textile, the wearable electronic textile further comprising a battery coupled to the textile substrate, wherein the battery is electrically coupled to a conductive yarn, the conductive yarn further electrically coupled to the sensor. The method further includes determining a movement of an actuator woven into the textile substrate, an amount of movement of an actuator woven into the textile substrate, or a combination thereof based on the sensor data, the actuator coupled to the conductive yarn. The method further includes transmitting a signal to the actuator to cause the actuator to change shape based on the determined movement, the determined amount of movement, or a combination thereof.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only exemplary aspects and are therefore not to be considered limiting of its scope, for the disclosure may admit to other equally effective aspects.

FIG. 1A schematically illustrates an example electronic textile according to at least one aspect of the present disclosure.

FIG. 1B is an image of an example electronic textile worn by a user according to at least one aspect of the present disclosure.

To facilitate understanding, identical reference numerals have been used, where possible, to designate identical elements that are common to the figures. It is contemplated that elements and features of one example may be beneficially incorporated in other examples without further recitation.

DETAILED DESCRIPTION

Figure 2:
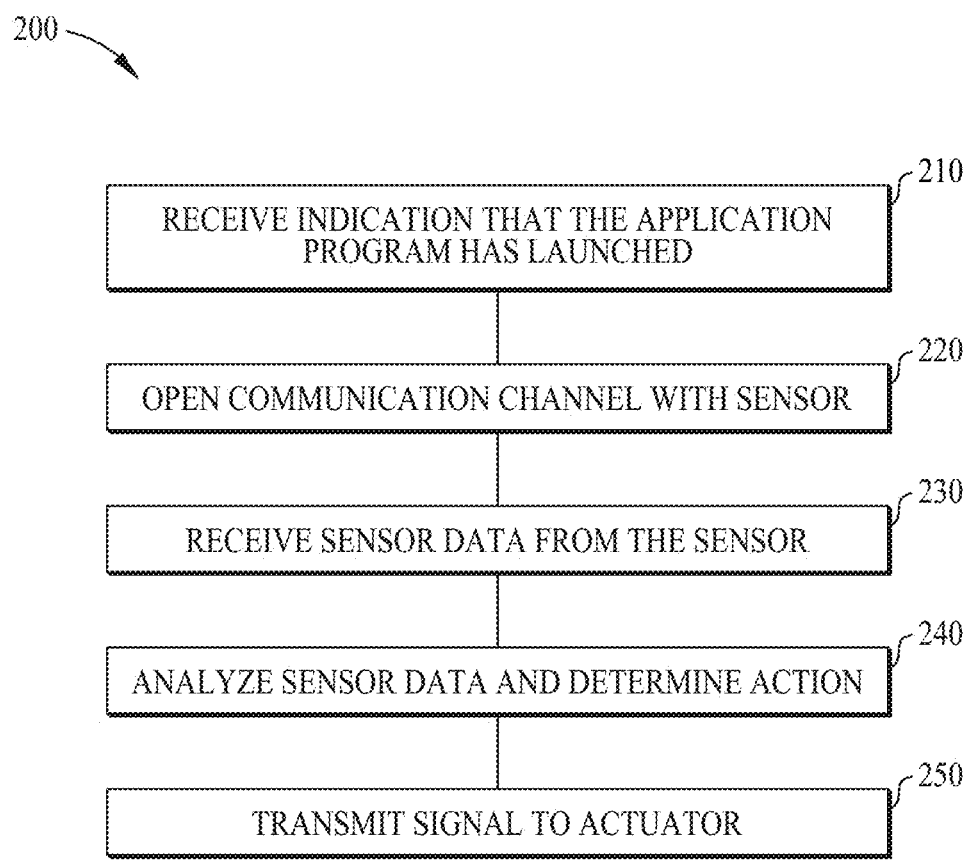
FIG. 2 is a flow chart of example operations for receiving sensor data and movement of the actuator(s).

Aspects of the present disclosure generally relate to electronic textiles and more specifically to self-sustaining, interactive electronic textiles and to systems incorporating such electronic textiles. The electronic textile can support human mobility by assisting the motion of the limbs and support improved posture. In addition, the electronic textile can help prevent blackout, panic attack, stress, and/or blood loss by, e.g., regulating blood circulation and take action based on a user's vital signs. Moreover, aspects described herein enable electronic textiles (e.g., wearables) with integrated intelligence that improves, e.g., the health and safety of the user/wearer. As described herein, the electronic textile exhibits various capabilities including data collection, information processing, and biosensing. The electronic textile is lightweight, acts rapidly, uses minimal power, and has advantageous mechanical properties such as flexibility, stretchability, and twistability.

Briefly, the electronic textile is a shape-variable textile having sensors embedded therein to monitor the physiological state of the user/wearer. The sensors can measure and monitor meaningful biological and/or physiological data from the wearer/user, e.g., heart rate, blood pressure and muscle fatigue. The electronic textile also includes actuators coupled thereto that change shape and/or stiffness in response to the sensor data. These actuators are stimulus responsive and reversibly actuatable. The actuators can respond to stimuli such as an electrical signal, electrical pulse, electrical field, magnetic field, temperature, and/or light, causing the electronic textile (or at least a portion of the electronic textile) to change shape, e.g., bend and/or compress based on, e.g., analysis of the wearer's/user's data.

By adjusting the shape of the actuators based on at least the sensor data, the electronic textile can, e.g., support intended motions of the wearer as well as regulate the wearer's blood circulation by squeeze/compress actions. Examples of intended motion include bending the arm during various activities such as eating, working, exercising, etc.

One or more components of the electronic textile are powered by batteries coupled to the electronic textile. Accordingly, and in some aspects, the electronic textile can be self-sustaining. The battery powers the sensor(s), processor(s), actuator(s), and other components such that the electronic textile can be free of an external power supply.

As described herein, the wearables enable real-time monitoring and collection of biological and/or physical data such as physiological stress (e.g., heart rate, body temperature, glucose level, oxygen) and environment. The data is analyzed and a decision is made based on the analysis. Accordingly, and in some aspects, the electronic textile includes one or more sensors such as electrocardiogram sensor, electromyogram sensor, electroencephalogram sensor, galvanic skin response sensor, haptic sensor, force sensor, oxygen sensor, electrochemical sensor, thermometer, skin impedance sensor, transpiration sensor, respiration sensor, or combinations thereof.

The electronic textile further includes a computing system. Additionally or alternatively, the computing system can be external to the textile in the form of, e.g., a smart phone, smart watch, or the like. One example computing system includes a processor and a memory including computer readable instructions. The processor is configured to, based on execution of the computer readable instructions, receive an indication from the electronic textile that the application program has started and receive sensor data from one or more of the sensors. For example, the one or more sensors provides information about what muscle is activated or inactivated during movement/motion, how much a user's skin temperature is increasing or decreasing during movement/motion, and/or how much a user's heart rate is increasing or decreasing during movement/motion. The processor is further configured to analyze sensor data, and make a decision based on, e.g., the sensor data. The processor can be further configured to transmit sensor data. Accordingly, and in certain aspects, transmitters and/or antennae can be a part of the electronic textile to transmit signals to another processor.

The following illustrative, but non-limiting, examples are put forth so as to provide those of ordinary skill in the art with a complete disclosure and description of how to make and use aspects of the present disclosure, and are not intended to limit the scope of aspects of the present disclosure. Efforts have been made to ensure accuracy with respect to numbers used (e.g. amounts, dimensions, etc.) but some experimental errors and deviations should be accounted for.

EXAMPLES

Example 1: Electronic Textile

FIG. 1A schematically illustrates an example electronic textile 100 according to at least one aspect of the present disclosure. The electronic textile 100 can perform mechanical work, such as changing shape, e.g., bending and/or compressing.

The electronic textile 100 includes a textile substrate 102 made of fabric. The fabric can be woven or non-woven, and formed from natural fibers, synthetic fibers, or a combination thereof. The electronic textile 100 includes actuator(s) 104 that are knit, sewn, woven, or otherwise incorporated into the electronic textile 100. The actuator(s) 104 are stimulus responsive and reversibly actuatable. The actuator(s) 104 can respond to stimuli such as an electrical signal, electrical pulse, electrical field, magnetic field, temperature, and/or light, causing the electronic textile 100 (or at least a portion of the electronic textile 100) to change shape, e.g., bend and/or compress.

The electronic textile 100 further includes one or more energy storage systems 106 (e.g., one or more batteries). The one or more batteries 106 supplies power or voltage to actuator(s) 104, sensor(s) 110, processor(s) 112, and/or other electronics and/or other elements of the electronic textile 100. The one or more batteries 106 can be made of flexible fibers that are weaved directly into the electronic textile 100. Conductive yarn(s) 108 (e.g., fabric, fibers, etc.) electrically couple the one or more batteries 106 with actuator(s) 104, sensor(s) 110, processor(s) 112, and/or other electronics of the electronic textile 100. Suitable signal transfer elements can also be incorporated in the electronic textile 100.

As discussed above, the textile substrate 102 is made of fabric formed from natural fibers, synthetic fibers, or a combination thereof. Illustrative, but non-limiting, examples of natural fibers include cellulosic fibers and proteinaceous fibers, e.g., wool, silk, cotton, and hemp. Synthetic fibers include, but are not limited to polymers (homopolymers or copolymers) made in a fiber or a filament form, such as polyamides including nylon (such as nylon 6 and nylon 66), Kevlar™, Twaron™, and Nomex™; polyolefins such as polypropylene; polyesters such as polyethylene terephtalate (PET); polyureas and block copolymers thereof such as polyurethaneureas; polyurethanes, including polyurethane block copolymers; polyethers, including polyether copolymers such as polyether-polyurea copolymers, e.g., Spandex™ or Lycra™; acrylics; synthetic cellulose-derived fibers such as rayon; and combinations thereof. The natural fibers, synthetic fibers, and combinations can be woven, non-woven, knitted, felted, thermally bonded, hydroentangled, spunbonded, meltblown, electrospun or formed by other nonwoven processes, or combinations of processes, into a fabric. In some aspects, the natural fibers, synthetic fibers, and combinations can be embedded and not woven/knitted.

The fabric can have voids, or a degree of porosity, to enable, e.g., penetration or wetting by the electrolyte, and to support the electroactive cathode/anode materials of the one or more batteries 106 and other components (e.g., actuator(s) 104, conductive yarn(s) 108, sensor(s) 110, processor(s) 112, etc.) of the electronic textile. These components can be coupled to (e.g., woven, knitted, embedded within, or otherwise incorporated with), the electronic textile 100. Illustrative, but non-limiting, examples of actuator(s), batteries, conductive yarn(s) 108, sensor(s) 110, processor(s) 112 that can be used as part of the electronic textile 100 or as part of a system incorporating the electronic textile 100 are discussed below.

In some aspects, the electronic textile 100 is a wearable article. In these and other aspects, the wearable article comprises a heart rate belt or band, or a garment, for example a shirt, a bra, a sports accessory, an undergarment, a sock, or a pair of pants. FIG. 1B shows an example use of the garment which can be worn, e.g., around an elbow to, e.g., support the elbow. Depending on the wearable article, the sensor(s) 110 are placed in a suitable location for measuring a physiological signal, e.g., close to the heart in a shirt for measuring the heart rate.

Example 2: Method

FIG. 2 is a flowchart of example operations 200 for receiving sensor data and moving of the actuator(s). Operations 200 are performed by a processor embedded in the electronic textile and/or a processor that is external to the electronic (e.g., in a smart phone, smart watch, etc.). Operation 200 begins at operation 210 where processor(s) (e.g., processor(s) 112) receive an indication that the application program launched. At operation 220, the processor(s) open a communication channel with one or more sensors (e.g., sensor(s) 110). In some examples, the communication channel is a user datagram protocol (UDP) connection between the processor(s) and the sensor. In other examples, the communication channel is a transmission control protocol (TCP) connection, and internet protocol (IP) connection or various other communication or data transfer protocols.

At operation 230, the processor(s) receive sensor data from the sensor over the established communication channel. In general, sensor data is of a format associated with the specific sensor. That is, each sensor transmits a signal (e.g., data) in a format unique to that sensor. At operation 240, the processor(s) analyze the sensor data and makes a determination as to an action, e.g., a movement of the actuator(s) (e.g., actuator(s) 104) —such as bending, stretching, compression, expansion, and/or relaxation—and/or an amount of movement of the actuator. At operation 250, the processor(s) transmit a signal to the actuator to cause the actuator to change shape based on the determined movement and the amount of movement.

In general, operations 200 represent a process for receiving sensor data from a single sensor and causing the actuator(s) to move based on the sensor data. However, operations 200 may be extended to support receiving sensor data from multiple sensors, by opening a communication channel for each sensor. Then, the processor(s) perform operations 200 for each sensor in parallel.

The operations 200 can be used in a method for supporting an intended motion of a user (or wearer), to assist with blood circulation a user (or wearer), to assist with respiration a user (or wearer), and many other applications. For example, after operation 250, the actuator changes shape, and in turn, the electronic textile changes shape—e.g., compresses, expands, etc. When, for example, the processor(s) makes a determination to increase blood circulation based on the sensor data, the electronic textile (or a portion of the electronic textile) can contract.

Example 3: Actuators for the Electronic Textile

The electronic textile 100 includes actuator(s) 104 that are coupled to (e.g., knit, sewn, woven, or otherwise incorporated into) the electronic textile 100. The actuator(s) 104 are stimulus responsive and reversibly actuatable. The actuator(s) 104 can respond to stimuli such as an electrical signal, electrical pulse, electrical field, magnetic field, temperature, and/or light, causing the actuator(s) 104 to do mechanical work, such as to change shape, e.g., bend and/or compress.

Illustrative, but non-limiting, examples of actuator(s) 104 include elastomers; liquid crystal elastomers; shape memory alloys (also known as smart alloys); shape memory polymers (which can be fiber-reinforced); electro-thermally driven shape-memory metal wires; polymer/carbon nanotube composite fibers; hybrid CNT muscles (in which a guest, such as paraffin wax is infiltrated into a twist-spun carbon nanotube yarn); electrochemically driven fibers of organic conducting polymers; polymeric electric field-driven electrostrictive rubbers and relaxor ferroelectrics; spring actuators; and combinations thereof. Liquid crystal elastomers are polymers having anisotropic properties. When liquid crystal elastomers are subjected to a stimulus, the liquid crystal mesogens within the elastomer can reorient in certain directions causing the elastomer to change its shape by, for example, bending, curling, and/or shrinking.

The incorporation of actuators into electronic textiles has been challenged by, e.g., the large amount of energy demanded by the actuator as well as the high temperatures utilized to cause the actuator to change shape. For example, many elastomers and shape memory alloys change shape in response to a temperature of about 60° C. Such elevated temperatures, however, could burn skin that touches the elastomer. In certain aspects, the electronic textile 100 described herein can include thermal insulating materials to alleviate such issues.

Elastomers are generally polymeric materials that can be deformed and are generally capable of withstanding elastic deformation. Suitable elastomers can include polymers, copolymers, composites, and/or mixtures of polymers and copolymers. Suitable elastomers or portions of elastomers that can be included in the actuator(s) 104 include thermoplastic elastomers, styrenic materials, olefin materials, polyolefins, polyurethane thermoplastic elastomers, polyamides, synthetic rubbers, polydimethylsiloxanes, polybutadienes, polystyrenes, polyisobutylenes, polybenzenes, ethylene-butadiene-styrenes, polyurethanes, polychloroprenes, polyfluorenes, polymer-containing hydrazines, fluorene-modified elastomers, derivatives thereof, or a combination thereof. Other elastomers, or portions of elastomers that can be additionally, or alternatively, included in the actuator(s) 104 can include polyesters, poly(lactic acid), poly(acrylonitrile-butadiene-styrene), poly(ethylene), poly(propylene), poly(caprolactone), poly(tetrafluoroethylene), poly(methyl methacrylate), polyether ether ketone (PEEK), poly(glycolic acid), poly(lactic-co-glycolic acid), poly(carbonate), poly (vinyl chloride), nylon, perfluoropolyethers, cyclic olefin copolymers, alginate, hyaluronic acid, cellulose, and other polysaccharides, thiol-ene elastomers, thiol-ene viscoelastic polymers, thiol-ene glassy polymers, terpene-derived poly (thioethers), poly(glycerol-co-sebacate), derivatives thereof, and/or a combination thereof. Non-limiting examples of elastomers or portions of elastomers that can be additionally, or alternatively, included in the actuator(s) 104 include elastomers made from monomers such as thiol-enes, acrylates, urethanes, siloxanes, azobenzenes, olefins, polyesters, and polycarbonates, derivatives thereof, or a combination thereof.

Dielectric elastomers may also be used such as silicon based composites that include one or more of graphene, carbon nanotubes, and/or metals. Silicone-TiO$_2$ composite elastomer is an illustrative, but non-limiting, dielectric elastomer.

In some aspects, the actuator(s) 104 comprises a precursor polymer fiber such as polyethylene, nylon fibers (e.g., nylon 6, nylon 6,6), polyvinylidene difluoride (PVDF), Kevlar™ polyester, and/or polypropylene. Other precursor polymer fibers can include styrenic materials, olefin materials, polyolefins, polyurethanes, polyamides, synthetic rubbers, polydimethylsiloxanes, polybutadienes, polystyrenes, polyisobutylenes, polybenzenes, ethylene-butadiene-styrenes, polyurethanes, polychloroprenes, polyfluorenes, polymer-containing hydrazines, fluorene-modified elastomers, derivatives thereof, or combinations thereof. Other precursor polymer fibers, or portions of precursor polymer fibers that can be additionally, or alternatively, included in the precursor polymer fibers can include polyesters, poly(lactic acid), poly(acrylonitrile-butadiene-styrene), poly(ethylene), poly(propylene), poly(caprolactone), poly(tetrafluoroethylene), poly(methyl methacrylate), polyether ether ketone (PEEK), poly(glycolic acid), poly(lactic-co-glycolic acid), poly(carbonate), poly(vinyl chloride), nylon, perfluoropolyethers, cyclic olefin copolymers, alginate, hyaluronic acid, cellulose, and other polysaccharides, thiol-ene elastomers, thiol-ene viscoelastic polymers, thiol-ene glassy polymers, terpene-derived poly(thioethers), poly(glycerol-co-sebacate), derivatives thereof, or combinations thereof. Non-limiting examples of precursor polymer fibers or portions of precursor polymer fibers that can be additionally, or alternatively, included in the actuator(s) 104 include elastomers made from monomers such as thiol-enes, acrylates, urethanes, siloxanes, azobenzenes, olefins, polyesters, and polycarbonates, derivatives thereof, or combinations thereof.

After the one or more precursor polymer fibers is selected, the one or more precursor polymer fibers are then coiled to form one or more actuator(s) 104. Coiling may be performed by twist insertion, twist-induced coiling, or mandrel coiling, as described below Twist insertion into the precursor polymer fiber can be accomplished by hanging a weight from one end of the fiber and attaching the other end of the fiber to the shaft of a motor. The attached weight is tethered against rotation so that each turn from the motor results in the addition of one turn to the fiber.

Twist-induced coiling can be performed by inserting a large amount of twist into the precursor polymer fiber such that fiber twist is at least partially converted to fiber writhe (e.g., coiling). Under a given load, coils spontaneously form when the inserted twist is above a critical twist density. This coiling typically occurs by coil nucleation at one or several nucleation points along the fiber, and then propagates from these nucleation points to the entire fiber. Loads applied during twist-induced coiling can range from about 0.3 MPa to about 700 MPa (or more) depending on, e.g., the type of fiber utilized and the diameter of the fiber utilized. The load can be adjusted at various stages of the twist-induced coiling procedure such as before coil nucleation and/or after coil nucleation. The load applied during coiling can also be used to tune the diameter of the coils. In addition, the amount of twist (in units of turns/meter (turns/m)) is also varied during the twist-induced coiling. The amount of twist can be adjusted at various stages of the twist-induced coiling procedure such as before coil nucleation and/or after coil nucleation. The amount of twist during twist-induced coiling can range from about 50 turns/m to about 5,000 turns/m (or more) depending on, e.g., the type of fiber utilized and the diameter of the fiber utilized. After sufficient twist is inserted to fully coil a fiber, further twist or untwist could be performed to change the spring index of the fiber.

For a nylon 6,6 monofilament sewing thread (~120-130 µm diameter), loads from about 14 MPa and about 20 MPa typically nucleate coils. See C. S. Haines et al., Science, 2014, Vol. 343, 868-872. After coil nucleation, the load can be adjusted across a wider range from about 10 MPa to about 35 MPa. The load applied during coiling was used to tune the diameter of the coils.

Specifically, and in some examples, a 127 µm nylon 6,6 monofilament sewing thread can be coiled by inserting twist at a load of about 15-17 MPa. About 1,800-2,000 turns/m of twist is used to induce nucleation in the nylon 6,6 monofilament, and about 2,900-3,100 turns/m of twist results in a fully coiled fiber. As another example, a 180 µm silver-plated nylon 6,6, multifilament fiber is coiled by inserting twist at a load of about 13-15 MPa. To induce nucleation in the silver-plated nylon 6,6, multifilament fiber, about 1,350-1,550 turns/m of twist is used, and about 2,300-2,500 turns/m of twist results in a fully coiled fiber. As another example, a 270 µm nylon 6 monofilament fiber is coiled by inserting twist at a load of about 16-18 MPa. About 750-950 turns/m of twist is used to induce nucleation in the nylon 6 monofilament fiber, and about 1,350-1,550 turns/m of twist results in a fully coiled fiber. As another example, a 130 µm fused polyethylene braid is coiled by inserting twist at a load of about 35-40 MPa. About 1,200-1,400 turns/m of twist is used to induce nucleation in the fused polyethylene braid, and about 2,200-2,400 turns/m of twist results in a fully coiled fiber.

Mandrel coiling can be performed by twisting a precursor polymer fiber and then wrapping the twisted fiber around a mandrel to form a coil. Annealing at above the maximum actuation temperature, but below the polymer melting point, allows the coil to retain shape after removal from the mandrel. Depending on the specific fiber, this heat-set temperature is typically between about 65° C. and about 240° C., and the coil is held at this temperature for about 1 hour or more. Heat setting can be performed under an atmosphere of argon or vacuum.

The actuator(s) 104 based on, e.g., metal wires, fishing lines, different fibers (as a thread) can be coupled to (e.g., knitted, sewn, weaved, or otherwise incorporated into) the electronic textile by using suitable sewing, weaving, or knitting machines.

Example 4: Battery for the Electronic Textile

The electronic textile 100 includes a lightweight and weavable energy storage system, e.g., one or more batteries 106. The one or more batteries 106 supplies power or voltage to actuator(s) 104, sensor(s) 110, and/or other elements of the electronic textile 100. The one or more batteries 106 can be weaved batteries. The one or more batteries 106 can be made of flexible fibers that are weaved directly into the electronic textile 100. As an example, battery electrodes can be co-drawn within a polymer fiber that is filled later with a liquid, solid, and/or gel electrolyte. As another example, a battery using lithium metal with nanostructures (such as nanotubes) can be, e.g., stitched or otherwise woven into the electronic textile 100.

In some examples, the one or more batteries 106 include a flexible lithium metal battery as disclosed in U.S. patent application Ser. No. 16/560,731, U.S. patent application Ser. Nos. 16/560,747, 15/665,171, which are hereby incorporated by reference herein in their entirety. In some aspects, the one or more batteries 106 include carbon nanotube-based yarns or fibers that make up at least a portion of the battery electrodes. One yarn is an anode and the other yarn is a cathode. When the yarns are woven, kitted, knotted, twisted, or otherwise coupled, in conjunction with an electrolyte, a battery can be formed. As an illustrative, but non-limiting, example, the one or more batteries 106 is a lithium ion battery having an anode, a cathode, a separator positioned between the anode and the cathode, and an electrolyte. The anode can include a composite material that includes anode active material (e.g., graphite, silicon, a porous material that matches or substantially matches the voltage of the given cathode material, natural graphite, artificial graphite, activated carbon, carbon black, high-performance powdered graphene, etc., and combinations thereof) particles in a three-dimensional cross-linked network of carbon nanotubes. The cathode can include a composite material that includes cathode active material (lithium metal oxide, lithium metal, etc.) particles in a three-dimensional cross-linked network of carbon nanotubes. According to some aspects, the three-dimensional cross-linked network of carbon nanotubes can have a webbed morphology, a non-woven, non-regular, or non-systematic morphology, or combinations thereof.

Metals in lithium metal oxides according to the present disclosure may include but are not limited to one or more alkali metals, alkaline earth metals, transition metals, aluminum, or post-transition metals, and hydrates thereof. Non-limiting examples of lithium metal oxides include lithiated oxides of Ni, Mn, Co, Al, Mg, Ti, and any mixture thereof. In an illustrative example, the lithium metal oxide is lithium nickel manganese cobalt oxide ($LiNi_xMn_yCo_zO_2$, $x+y+z=1$), $Li(Ni,Mn,Co)O_2$, or Li—Ni—Mn—Co—O. The lithium metal oxide powders can have a particle size defined within a range between about 1 nanometer (nm) and about 100 microns ($\mu m$), or any integer or subrange in between. In a non-limiting example, the lithium metal oxide particles have an average particle size of about 1 $\mu m$ to about 10 $\mu m$.

Carbon nanotubes suitable for use in the methods of the present disclosure include single-walled nanotubes, few-walled nanotubes, and multi-walled nanotubes. In some aspects, the carbon nanotubes are single-walled nanotubes. Few-walled nanotubes and multi-walled nanotubes may be synthesized, characterized, co-deposited, and collected using any suitable methods and apparatuses known to those of ordinary skill in the art, including those used for single-walled nanotubes. The carbon nanotubes may range in length from about 50 nm to about 10 cm or greater.

Suitable separator materials include those known to persons of ordinary skill in the art for use in between battery anodes and cathodes, to provide a barrier between the anode and the cathode while enabling the exchange of lithium ions from one side to the other, such as a membranous barrier or a separator membrane. Suitable separator materials include, but are not limited to, polymers such as polypropylene, polyethylene and composites of them, as well as PTFE. The separator membrane is permeable to lithium ions, allowing them to travel from the cathode side to the anode side and back during the charge-discharge cycle. But the separator membrane is impermeable to anode and cathode materials, preventing them from mixing, touching and shorting the battery. The separator membrane also serves as electrical insulator for metal parts of the battery (leads, tabs, current collectors, metal parts of the enclosure, etc.) preventing them from touching and shorting. The separator membrane also prevents flows of the electrolyte.

In some aspects, the separator is a thin (about 15-25 $\mu m$) polymer membrane (tri-layer composite: polypropylene-polyethylene-polypropylene, commercially available) between two relatively thick (about 20-1000 $\mu m$) porous electrode sheets. The thin polymer membrane may be about 15-25 $\mu m$ thick, such as 15-23, 15-21, 15-20, 15-18, 15-16, 16-25, 16-23, 16-21, 16-20, 16-18, 18-25, 18-23, 18-21, 18-20, 20-25, 20-23, 20-21, 21-25, 21-23, 23-25, 15, 16, 17, 18, 19, 20, 21, 22, 23, 24, or 25 $\mu m$ thick, or any integer or subrange in between. The two relatively thick porous electrode sheets may each independently be 50-500 $\mu m$ thick, such as 50-450, 50-400, 50-350, 50-300, 50-250, 50-200, 50-150, 50-100, 50-75, 50-60, 50-55, 55-500, 55-450, 55-400, 55-350, 55-300, 55-250, 55-200, 55-150, 55-100, 55-75, 55-60, 60-500, 60-450, 60-400, 60-350, 60-300, 60-250, 60-200, 60-150, 60-100, 60-75, 75-500, 75-450, 75-400, 75-350, 75-300, 75-250, 75-200, 75-150, 75-100, 100-500, 100-450, 100-400, 100-350, 100-300, 100-250, 100-200, 100-150, 150-500, 150-450, 150-400, 150-350, 150-300, 150-250, 150-200, 200-500, 200-450, 200-400, 200-350, 200-300, 200-250, 250-500, 250-450, 250-400, 250-350, 250-300, 300-500, 300-450, 300-400, 300-350, 350-500, 350-450, 350-400, 400-500, 400-450, 450-500, 50, 55, 60, 75, 100, 150, 200, 250, 300, 350, 400, 450, or 500 $\mu m$, or any integer or subrange in between.

The electrolyte is a gel and/or a solid electrolyte. The electrolyte can include one or more polymers and/or lithium based materials. Illustrative, but non-limiting, examples of electrolytes and components of electrolytes include poly (ethylene oxide) (PEO), poly(propylene oxide)(PPO), poly (vinyl alcohol) (PVA), poly(vinylidene fluoride) (PVDF), poly(acrylonitrile) (PAN), poly(vinyl chloride) (PVC), poly (methyl methacrylate) (PMMA), hexafluoropropylene (HFP), and poly(ethyl α-cyanoacrylate) (PECA); monomers or polymers of ethylene carbonate (EC), propylene carbonate, dimethyl carbonate (DMC), diethylcarbonate (DEC), dimethylformamide (DMF), dimethylsulfoxide (DMSO), butyrolactone (BL), gamma-butyrolactone (γ-BL), and 2-methyl-2-oxazoline; and lithium-based materials such as $LiClO_4$, $LiCF_3SO_3$, $LiBF_4$, and $LiN(CF_3SO_2)_2$. Combinations of the aforementioned materials can be used as well as copolymers of the aforementioned materials can be used. Examples of polymer gel electrolytes that can be used include PAN-EC/PC/DMF-$LiClO_4$, PMMA-EC/PC-$LiClO_4$, PAN-EC/PC-$LiClO_4$, PVC-EC/PC-$LiClO_4$, PAN-EC/PC-$LiCF_3SO_3$, PAN-EC/DEC-$LiClO_4$, PVDF-EC/PC-$LiBF_4$, PVDF-HFP-EC/DEC-$LiN(CF_3SO_2)_2$, PMMA-EC/PC/γ-BL-$LiCF_3SO_3$, and PMMA-EC/DMC-$LiN(CF_3SO_2)_2$.

The cathode, anode, separator, and electrolyte is extrudable and/or drawable into fibers which are compatible with weaving processes. The one or more batteries 106 is woven into a textile (e.g., textile substrate 102) and connected to conductive thread(s) or conductive yarn(s). The battery can be inside a flexible pouch as described in U.S. Patent Application Publication 2020/0083560, which is hereby incorporated by reference herein in its entirety. In such cases, the flexible pouch (encasing the battery) can be attached to the textile by, e.g., placing the pouch in a woven pocket of the electronic textile.

In some aspects, the one or more batteries 106 can take the form of a coaxial cable-like formation where the electrodes are cylindrical shape. Such a battery can then be woven into the electronic textile via knitting/sewing machines.

In some aspects, the one or more batteries 106 can be formed by sequentially winding aligned carbon nanotube composite yarn cathode and anode onto a cotton fiber. In an example, the cathode includes a carbon nanotube lithium manganate (CNT-LMO) composite yarn, and the anode includes a silicon-coated CNT sheet disposed between two CNT sheets (denoted as CNT-Si/CNT composite yarn). The battery further includes a gel electrolyte. Cable or yarn like batteries can be woven into the textile using typical knitted woven machines or can be sewed.

In some aspects, the one or more batteries can be coated or covered with a protective layer, such as an insulator material like a polymer. The insulator material can be flexible. The one or more batteries 106 can be coupled to (e.g., knitted, sewn, weaved, or otherwise incorporated into) the electronic textile by using suitable sewing, weaving, or knitting machines.

Example 5: Conductive Yarns for the Electronic Textile

The electronic textile 100 includes conductive yarns/wires 108 (e.g., fabric, fibers, etc.) to electrically couple the one or more batteries 106 with the sensor(s) 110, actuator(s) 104, processor(s) 112, or other electronics of the electronic textile 100. In some examples, the conductive yarn/wire 108 is a conductive yarn/wire as disclosed in U.S. patent application Ser. No. 16/446,389, which is hereby incorporated by reference herein in its entirety.

In some aspects, the conductive yarns 108 include a non-conductive or less conductive substrate which is coated, embedded, and/or impregnated with electrically conductive elements, such as carbon, nickel, copper, gold, silver, titanium, or conductive polymers (e.g., polythiophenes such as poly(3,4-ethylenedioxythiophene) (PEDOT); polyanilines; polypyrroles; polyacetylenes; polystyrenesulfonates; or combinations thereof). The conductive polymers can be doped, with, e.g., dinonylnaphthalene sulfonic acid (DNNSA), dodecylbenzene sulfonic acid, camphorsulfonic acid, dibutylnaphthalene sulfonic acid, polystyrene sulfonic acid, or combinations thereof.

Metals and/or carbon can be applied to the non-conductive or less conductive substrate by any suitable technique such as chemical deposition, physical vapor deposition, and/or printed with conductive nanoparticle inks. Illustrative, but non-limiting, examples of the non-conductive or less conductive substrate include cotton, nylon, polyesters, polyamides, polyethylenes, polyphenylene benzobisoxazoles (PBO), and combinations thereof.

Example conductive yarns include, but are not limited to, silver-coated polyethylene, gold-coated polyethylene, silver-coated polyamides, carbon fibers, conductive stainless steel fiber.

Conductive yarns 108 can be coupled to (e.g., knitted, sewn, weaved, or otherwise incorporated into) the electronic textile by using suitable sewing, weaving, or knitting machines.

Example 6: Processors, Sensors, and Electronics for the Electronic Textile

As described above, one or more sensor(s) 110 are embedded within the electronic textile 100. The one or more sensor(s) 110 measure and/or monitor a physiological state of the user/wearer. Illustrative, but non-limiting, examples of sensor(s) 110 that can be embedded within the electronic textile 100 include electrocardiogram sensor, electromyogram sensor, electroencephalogram sensor, galvanic skin response sensor, haptic sensor, force sensor, oxygen sensor, electrochemical sensor, thermometer, skin impedance sensor, transpiration sensor, respiration sensor, or combinations thereof.

Processor(s) 112 are incorporated in the electronic textile 100. Additionally, or alternatively, processor(s) 112 can be located externally to the electronic textile 100. For example, at least one processor may be part of a smart phone or smart watch. The processor(s) 112 receive sensor data, analyze the sensor data, and make a determination as to, e.g., the movement of the actuator(s) 104 (such as bending, stretching, compression, and/or relaxation) and/or the amount of movement. In some aspects, the electronic textile further includes an element (e.g., an antenna) to transmit a signal to an external processor (located in, e.g., a smart phone, smart watch, etc.) or receive a signal from the external processor. The signal can come from the sensor(s) 110 of the electronic textile. The sensor signal can cause motion of the actuator(s) 104.

Sensor(s) 110, processor(s) 112, and/or other electronics can be coupled to (e.g., knitted, sewn, weaved, or otherwise incorporated into) the electronic textile by using suitable sewing, weaving, and knitting machines.

Example 7: Fabrication of an Example Electronic Textile

Example 7.A. Formation of Elastomer

Fabrication of LCE ink. An exemplary LCE ink can be prepared by the following procedure. A diacrylate mesogen, 1,4-bis-[4-(3-acryloyloxypropyloxy)benzoyloxy]-2-methylbenzene, is diluted in toluene and combined with a dithiol flexible spacer, 2,2'-(ethylenedioxy)diethanethiol, and a tetra-functional thiol cross-linker, pentaerythritol tetrakis (3-mercaptopropionate). A photo-initiator, 2-hydroxy-2-methylpropiophenone, is also added to permit the second-stage UV-cross-linking reaction. Next, about 2 wt % nanoclay is added (nanoclay, surface modified) to modify the viscosity of the LCE resin for DIW printing. Then, about 3 wt % dipropylamine, in a ~1:20 ratio with toluene, is added to trigger the first-stage cross-linking reaction. The LCE ink is ready for use.

Fabrication of Liquid Crystal Elastomer (LCE) Fiber. In this example, the LCE is prepared in a three-operation procedure. The LCE ink is first extruded through a direct ink write (DIW) printing nozzle via pressure applied by a regulator onto a rotating mandrel driven by a stepper motor (operation 1). In DIW printing, a liquid resin, or slightly crosslinked elastomer, is extruded through a nozzle to form a three-dimensional structure. In operation 1, the ink is extruded using a pressure of 50 psi, the nozzle is moved in the x-direction at about 5 mm/s, and the mandrel rotated at about 1 mm/s. The DIW printing nozzle can be placed approximately 2 mm from the substrate to generate an equidimensional line.

A first-stage curing of the printed fibers is then performed by using convective heating from a heater set to about 80° C. for about 10 minutes while the mandrel rotated (operation 2). Then, the pre-cured fibers are stretched between two mandrels rotating at different speeds to stretch the fiber and align the liquid crystal elastomer (LCE) mesogens followed by ultraviolet (UV) curing—the second-stage curing—to fix the LCE mesogen alignment (operation 3). In operation 3, and just prior to being rolled onto the second mandrel, the LCE fiber is photocured to fix the LCE mesogen alignment by using a 365 nm UV light source at an intensity of ~10 $mW/cm^2$, measured at the location of the LCE fiber, ~150 mm from the UV light source. The total UV curing time is about 2.5 minutes. By adjusting the nozzle speeds, mandrel movement speeds, extrusion pressure, and/or the nozzle size, LCE fibers with various diameters and actuation strains can be formed.

Example 7.B. Formation of Battery

Spinnable carbon nanotube (CNT) arrays are synthesized by chemical vapor deposition. A general procedure for forming spinnable CNTs includes depositing an aluminum oxide film on a $SiO_2$ substrate, and depositing a catalyst such as Fe, Mo or Mo/Fe on top of the aluminum oxide film. The substrate is then heated to a suitable temperature of from about 500° C. to about 950° C., such as from about 700° C.

to about 950° C. One or more hydrocarbon sources (e.g., $CH_4$, $C_2H_2$, or other source) with a carrier gas (e.g., $H_2$ and/or Ar) to form the CNTs. Aligned CNT sheets are then continuously dry-drawn from the array with widths up to centimeters and lengths of meters. For the cathode, lithium manganate (LMO) particles are directly deposited onto the aligned CNT sheet, followed by scrolling into a CNT-LMO composite yarn. For the anode, a hybrid-structure is utilized. Here, silicon is coated onto a CNT sheet by electron beam evaporation. The Si-coated CNT sheet is then sandwiched between two bare CNT sheets and further scrolled into a composite yarn with the designed hybrid layered structure (denoted as CNT-Si/CNT composite yarn). Thus, the CNT-LMO and CNT-Si/CNT composite yarns served as cathode and anode in the full cell, respectively.

The gel electrolyte is made as follows. 1 M $LiClO_4$ solution in ethylene carbonate/diethyl carbonate (50/50, v/v) is first prepared. About 0.8 g of poly(vinylidene fluoride-co-hexafluoropropylene) (PVDF-HFP) is dissolved in ~12 mL of tetrahydrofuran and the $LiClO_4$ is mixed with PVDF-HFP solution at a volume ratio of about 1/6. After stirring for about 12 h, a clear solution is obtained and vacuum-dried to remove the solvent to form a gel electrolyte.

The CNT-LMO composite yarn is prepared by the following procedure. Lithium manganate (LMO) nanoparticles are synthesized by a hydrothermal method. LiOH (0.377 g) and $MnO_2$ (1.37 g) as first dissolved in $H_2O$ (40 mL), followed by adding glucose (0.2 g) and $H_2O$ (40 mL), and reacted at 200° C. for 24 h. The resulting solid products is filtered and washed with distilled water and ethanol for at least three times. The as-synthesized lithium manganate (LMO) nanoparticles are then dispersed in N-methyl pyrrolidinone to form a suspension (concentration of 5 mg mL-1) through an ultrasonic treatment for 1 h. The suspension is then deposited onto the aligned carbon nanotube (CNT) sheet. The CNT-LMO composite yarn is then scrolled from the above LMO-deposited CNT sheet. The CNT-Si/CNT composite yarn is prepared by a similar process with the formation of an Archimedean scroll.

In this example, a cotton fiber is used as the substrate that has been further covered with a shrinkable tube as a protecting layer. The CNT-LMO composite yarn is wound onto the cotton fiber. Afterwards, the gel electrolyte with the solvent of tetrahydrofuran is coated onto the sample, followed by evaporation of the solvent. The coating process was repeated for three times to produce a thick gel electrolyte, followed by winding the CNT-Si/CNT composite yarn. After drying in vacuum at about 60° C. for about 5 h, the sample was transferred to an argon-filled glovebox with both moisture and oxygen to be less than 1 about ppm. For packaging, the sample can be inserted into another shrinkable tube as a packaging layer while both open ends are sealed by polydimethylsiloxane, which could be hardened at room temperature for about 2 h.

ASPECTS LISTING

The present disclosure provides, among others, the following aspects, each of which can be considered as optionally including any alternate aspects:

Clause 1. A system to assist with an intended motion of a user, comprising: one or more processors; and an electronic textile, comprising: a textile substrate; an actuator coupled to the textile substrate; a sensor coupled to the textile substrate; and a battery coupled to the textile substrate, the battery electrically coupled to a conductive yarn, the conductive yarn further electrically coupled to the actuator and the sensor.

Clause 2. The system of Clause 1, wherein at least one of the one or more processors is coupled to in the textile substrate.

Clause 3. The system of Clause 1 or Clause 2, wherein at least one of the one or more processors is external to the textile substrate.

Clause 4. The system of Clause 3, wherein the electronic textile further comprises an element to transmit a signal to the external processor or to receive a signal from the external processor.

Clause 5. The system of any one of Clauses 1-4, further comprising a memory including computer readable instructions, wherein the one or more processors is configured to, based on execution of the computer readable instructions: receive an indication from a program application that the program application has started; receive sensor data from the sensor; analyze the sensor data; determine a movement of the actuator, an amount of movement of the actuator, or a combination thereof; and transmit a signal to the actuator to cause the actuator to change shape based on the determined movement, the determined amount of movement, or a combination thereof.

Clause 6. The system of any one of Clauses 1-5, wherein the battery comprises: an electrolyte comprising a gel, a solid, or a combination thereof; a flexible anode comprising a composite material comprising anode active material particles in a three-dimensional cross-linked network of carbon nanotubes; a flexible cathode comprising a composite material cathode active material particles in a three-dimensional cross-linked network of carbon nanotubes; and a flexible separator membrane positioned between the flexible anode and the flexible cathode.

Clause 7. The system of any one of Clauses 1-6, wherein the sensor comprises an electrocardiogram sensor, an electromyogram sensor, an electroencephalogram sensor, a galvanic skin response sensor, a haptic sensor, a force sensor, an oxygen sensor, an electrochemical sensor, a thermometer, a skin impedance sensor, a transpiration sensor, a respiration sensor, or combinations thereof.

Clause 8. The system of any one of Clauses 1-7, wherein the actuator causes at least a portion of the electronic textile to bend, stretch, compress, expand, or relax.

Clause 9. The system of any one of Clauses 1-8, wherein the electronic textile is a heart rate belt, a band, or a garment.

Clause 10. The system of any one of Clauses 1-9, wherein the electronic textile a wearable article.

Clause 11. The system of Clause 10, wherein the wearable article is a garment selected from the group consisting of a shirt, a bra, a sports accessory, an undergarment, a sock, and a pair of pants.

Clause 12. A system to assist with blood circulation of a user, comprising: one or more processors; and a wearable electronic textile, comprising: a textile substrate; a contractable or expandable actuator coupled to the textile substrate; a sensor coupled to the textile substrate; and a battery coupled to the textile substrate, the battery electrically coupled to a conductive yarn, the conductive yarn further electrically coupled to the actuator and the sensor.

Clause 13. The system of Clause 12, wherein when the actuator contracts, at least a portion of the wearable electronic textile contracts, and the blood circulation of the user increases.

Clause 14. The system of Clause 12 or Clause 13, wherein at least one of the one or more processors is external to the textile substrate.

Clause 15. The system of Clause 14, wherein the wearable electronic textile further comprises an element to transmit a signal to the external processor or to receive a signal from the external processor.

Clause 16. The system of any one of Clauses 12-15, further comprising a memory including computer readable instructions, wherein the one or more processors is configured to, based on execution of the computer readable instructions: receive an indication from a program application that the program application has started; receive sensor data from the sensor; analyze the sensor data; determine a movement of the actuator, an amount of movement of the actuator, or a combination thereof; and transmit a signal to the actuator to cause the actuator to change shape based on the determined movement, the determined amount of movement, or a combination thereof.

Clause 17. The system of any one of Clauses 12-16, wherein the battery comprises: an electrolyte comprising a gel, a solid, or a combination thereof; a flexible anode comprising a composite material comprising anode active material particles in a three-dimensional cross-linked network of carbon nanotubes; a flexible cathode comprising a composite material cathode active material particles in a three-dimensional cross-linked network of carbon nanotubes; and a flexible separator membrane positioned between the flexible anode and the flexible cathode.

Clause 18. The system of any one of Clauses 12-17, wherein the sensor comprises an electrocardiogram sensor, an electromyogram sensor, an electroencephalogram sensor, a galvanic skin response sensor, a haptic sensor, a force sensor, an oxygen sensor, an electrochemical sensor, a thermometer, a skin impedance sensor, a transpiration sensor, a respiration sensor, or combinations thereof.

Clause 19. A method of assisting blood circulation of a user, comprising: analyzing sensor data from a sensor coupled to a textile substrate of a wearable electronic textile, the wearable electronic textile further comprising a battery coupled to the textile substrate, wherein the battery is electrically coupled to a conductive yarn, the conductive yarn further electrically coupled to the sensor; determining a movement of an actuator woven into the textile substrate, an amount of movement of an actuator woven into the textile substrate, or a combination thereof based on the sensor data, the actuator coupled to the conductive yarn; and transmitting a signal to the actuator to cause the actuator to change shape based on the determined movement, the determined amount of movement, or a combination thereof.

Clause 20. The method of Clause 19, wherein the sensor data includes a blood pressure signal of the user.

Aspects described herein include self-sustaining, interactive electronic textiles, to systems incorporating such electronic textiles, and to uses thereof. The electronic textile is self-powered. The electronic textile can support human mobility and posture as well as prevent (or at least mitigate) injury. The electronic textile includes batteries, sensors to monitor, e.g., heart rate, blood pressure, and/or muscle fatigue, as well as actuators that can support the intended motion of the person as well as regulate, e.g., blood circulation by squeeze/compression actions.

All documents described herein are incorporated by reference herein, including any priority documents and/or testing procedures to the extent they are not inconsistent with this text. Further, all documents and references cited herein, including testing procedures, publications, patents, journal articles, etc. are herein fully incorporated by reference for all jurisdictions in which such incorporation is permitted and to the extent such disclosure is consistent with the description of the present disclosure. As is apparent from the foregoing general description and the specific aspects, while forms of the aspects have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever an element or a group of elements is preceded with the transitional phrase "comprising," it is understood that we also contemplate the same element or group of elements with transitional phrases "consisting essentially of," "consisting of," "selected from the group of consisting of," or "Is" preceding the recitation of the element, or elements and vice versa.

The term "coupled" is used herein to refer to elements that are either directly connected or indirectly connected through one or more intervening elements. For example, a battery can be directly connected to the sensor, or it can be connected to the sensor via intervening elements.

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, aspects comprising "a monomer" include aspects comprising one, two, or more monomers, unless specified to the contrary or the context clearly indicates only one monomer is included.

Various aspects of the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and other circuit elements that are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software module(s) stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Additionally, or alternatively, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

While the foregoing is directed to aspects of the present disclosure, other and further aspects of the disclosure may be devised without departing from the basic scope thereof, and the scope thereof is determined by the claims that follow.

What is claimed is:

1. A system to assist with an intended motion of a user, comprising:
    one or more processors; and
    an electronic textile, comprising:
        a textile substrate;
        an actuator coupled to the textile substrate;
        a sensor coupled to the textile substrate; and
        a woven battery weaved into the textile substrate, the woven battery electrically coupled to a conductive yarn, the conductive yarn further electrically coupled to the actuator and the sensor, the woven battery comprising:
            woven anode and cathode yarns, the cathode yarns comprising lithium oxide particles, lithium metal particles, or combinations thereof on carbon nanotube-based fibers, the anode yarns comprising carbon nanotube-based fibers; and
            an electrolyte deposited onto the woven anode and cathode yarns,
        wherein, in response to a signal from the one or more processors, the actuator is configured to cause at least a portion of the electronic textile to bend, stretch, compress, expand, or relax.

2. The system of claim 1, wherein at least one of the one or more processors is coupled to the textile substrate.

3. The system of claim 1, wherein at least one of the one or more processors is external to the textile substrate.

4. The system of claim 3, wherein the electronic textile is configured to transmit a signal to an external processor or to receive a signal from the external processor.

5. The system of claim 1, further comprising a memory including computer readable instructions, wherein the one or more processors is configured to, based on execution of the computer readable instructions:
    receive an indication from a program application that the program application has started;
    receive sensor data from the sensor;
    analyze the sensor data;
    determine a movement of the actuator, an amount of movement of the actuator, or a combination thereof; and
    transmit a signal to the actuator to cause the actuator to change shape based on the determined movement, the determined amount of movement, or a combination thereof.

6. The system of claim 1, wherein the sensor comprises an electrocardiogram sensor, an electromyogram sensor, an electroencephalogram sensor, a galvanic skin response sensor, a haptic sensor, a force sensor, an oxygen sensor, an electrochemical sensor, a thermometer, a skin impedance sensor, a transpiration sensor, a respiration sensor, or combinations thereof.

7. The system of claim 1, wherein the electronic textile is a heart rate belt, a band, or a garment.

8. The system of claim 1, wherein the electronic textile is a wearable article.

9. The system of claim 8, wherein the wearable article is a garment selected from a group consisting of a shirt, a bra, a sports accessory, an undergarment, a sock, and a pair of pants.

10. The system of claim 1, wherein the anode yarns further comprise graphite, silicon, activated carbon, carbon black, powdered graphene, or combinations thereof on the carbon nanotube-based fibers of the anode yarns.

11. The system of claim 1, wherein the lithium oxide particles comprise lithiated oxides of a metal comprising Ni, Mn, Co, Al, Mg, Ti, or combinations thereof.

12. The system of claim 1, wherein the actuator comprises a liquid crystal elastomer.

13. A system to assist with blood circulation of a user, comprising:
one or more processors; and
a wearable electronic textile, comprising:
a textile substrate;
a contractable or expandable thread-based actuator coupled to the textile substrate;
a sensor coupled to the textile substrate; and
a woven battery weaved into the textile substrate, the woven battery electrically coupled to a conductive yarn, the conductive yarn further electrically coupled to the actuator and the sensor, the woven battery comprising:
woven anode and cathode yarns, the anode yarns comprising graphite, silicon, activated carbon, carbon black, powdered graphene, or combinations thereof on carbon nanotube-based fibers, the cathode yarns comprising lithium oxide particles, lithium metal particles, or combinations thereof on carbon nanotube-based fibers; and
an electrolyte deposited onto the woven anode and cathode yarns,
wherein, in response to a signal from the one or more processors, the actuator is configured to cause at least a portion of the electronic textile to bend, stretch, compress, expand, or relax.

14. The system of claim 13, wherein when the actuator contracts, at least a portion of the wearable electronic textile contracts, and the blood circulation of the user increases.

15. The system of claim 13, wherein at least one of the one or more processors is external to the textile substrate.

16. The system of claim 15, wherein the wearable electronic textile is configured to transmit a signal to an external processor or to receive a signal from the external processor.

17. The system of claim 13, further comprising a memory including computer readable instructions, wherein the one or more processors is configured to, based on execution of the computer readable instructions:

receive an indication from a program application that the program application has started;
receive sensor data from the sensor;
analyze the sensor data;
determine a movement of the actuator, an amount of movement of the actuator, or a combination thereof; and
transmit a signal to the actuator to cause the actuator to change shape based on the determined movement, the determined amount of movement, or a combination thereof.

18. The system of claim 13, wherein the sensor comprises an electrocardiogram sensor, an electromyogram sensor, an electroencephalogram sensor, a galvanic skin response sensor, a haptic sensor, a force sensor, an oxygen sensor, an electrochemical sensor, a thermometer, a skin impedance sensor, a transpiration sensor, a respiration sensor, or combinations thereof.

19. A method of assisting blood circulation of a user, comprising:
analyzing sensor data from a sensor coupled to a textile substrate of a wearable electronic textile, the wearable electronic textile further comprising a woven battery weaved into the textile substrate, the woven battery electrically coupled to a conductive yarn, the conductive yarn further electrically coupled to the sensor, the woven battery comprising:
woven anode and cathode yarns, the anode yarns comprising graphite, silicon, activated carbon, carbon black, powdered graphene, or combinations thereof on carbon nanotube-based fibers, the cathode yarns comprising lithium oxide particles, lithium metal particles, or combinations thereof on carbon nanotube-based fibers; and
an electrolyte deposited onto the woven anode and cathode yarns;
determining a movement of an actuator woven into the textile substrate, an amount of movement of an actuator woven into the textile substrate, or a combination thereof based on the sensor data, the actuator coupled to the conductive yarn; and
transmitting a signal from one or more processors via the textile substrate to the actuator to cause the actuator to change shape based on the determined movement, the determined amount of movement, or a combination thereof, thereby causing at least a portion of the electronic textile to change shape.

20. The method of claim 19, wherein the sensor data includes a blood pressure signal of the user.

* * * * *